United States Patent [19]
Ebner et al.

[11] Patent Number: 6,110,177
[45] Date of Patent: *Aug. 29, 2000

[54] APPARATUS AND METHOD FOR HARVESTING BONE

[75] Inventors: Peter R. Ebner; David E. Altobelli, both of Hollis, N.H.

[73] Assignee: Maxilon Laboratories, Inc., Hollis, N.H.

[*] Notice: This patent is subject to a terminal disclaimer.

[21] Appl. No.: 08/686,333

[22] Filed: Jul. 25, 1996

Related U.S. Application Data

[63] Continuation-in-part of application No. 08/537,303, Sep. 29, 1995, Pat. No. 5,683,406.

[51] Int. Cl.⁷ .................................................. A61B 17/32
[52] U.S. Cl. ........................... 606/84; 606/170; 606/167; 600/570

[58] Field of Search ..................... 606/84, 170, 167; 128/757, 758; 600/570, 571

[56] References Cited

U.S. PATENT DOCUMENTS

| | | | |
|---|---|---|---|
| 2,876,777 | 3/1959 | Kees, Jr. | 128/304 |
| 4,600,005 | 7/1986 | Hendel | 606/84 |

*Primary Examiner*—Michael H. Thaler
*Attorney, Agent, or Firm*—Hayes, Soloway, Hennessey, Gorssman & Hage, PC

[57] ABSTRACT

An instrument for harvesting bone comprises an elongate body having a hollow, and a proximal end and a distal end communicating with one another through the hollow. A blade having a curved cutting edge for cutting or abrading bone is mounted adjacent an aperture in the distal end. The cut or abraded bone moves through the aperture and into the hollow.

21 Claims, 8 Drawing Sheets

APPARATUS AND METHOD FOR HARVESTING BONE

This application is, in part, a continuation of our application Ser. No. 08/537,303 filed Sep. 29, 1995 now U.S. Pat. No. 5,683,406. The discussion of the prior art and the complete disclosure of this parent application is incorporated herein by references.

TECHNICAL FIELD

The present invention relates to the field of surgery and more particularly to removal of surface bone for application as autogenous bone grafts.

PRIOR ART

As discussed more fully in the parent application, numerous procedures and devices have been employed for harvesting bone for application as autogenous bone grafts. However, none have been satisfactorily simple or effective to collect, preserve, or treat the bone for such grafting.

SUMMARY OF THE INVENTION

The invention is directed to a hand-held surgical instrument for the cutting, removal, and storage of bone surface shavings for use as autogenous bone grafts. The instrument is comprised of a blade mounted in a handle for holding and supporting said blade. The blade has a cutting structure adjacent its distal end in the form of a sharpened loop. The loop's wedge shaped cross-section is defined proximally by a perpendicular curved aperture through the blade, and distally by ground and honed relief. In the preferred form, the handle cooperates to provide a storage space adjacent the distal end of the blade for receiving harvested bone from the cutting structure. This manual instrument is held at an acute angle to the bone, and with minimal downward pressure, is drawn across the bone surface to cut and collect a thin shaving of bone. The blade is preferably retractable to allow the clinician access to the harvested material. A plunger is incorporated into the handle to serve both as a locking mechanism to secure the blade and as a means to advance and consolidate the bone in the distal aspect of the instrument.

BRIEF DESCRIPTION OF THE DRAWINGS

FIG. 2 shows side (2B), top (2A, 2E, 2F), bottom (2C), and sectional (2D) views of the handle.

FIG. 3 shows side (3B), top (3A), bottom (3C), and sectional (3D) views of the plunger.

FIG. 4 shows top (4A), side (4B), and end (4C) view of the blade.

FIG. 5 shows enlarged top (5A) and sectional (5B) views of the distal (cutting) end of the blade.

FIG. 7 illustrates the use of the instrument to collect (7A), mix (7B) and apply (7C) bone shavings.

DETAILED DESCRIPTION OF THE INVENTION

Figure 1:
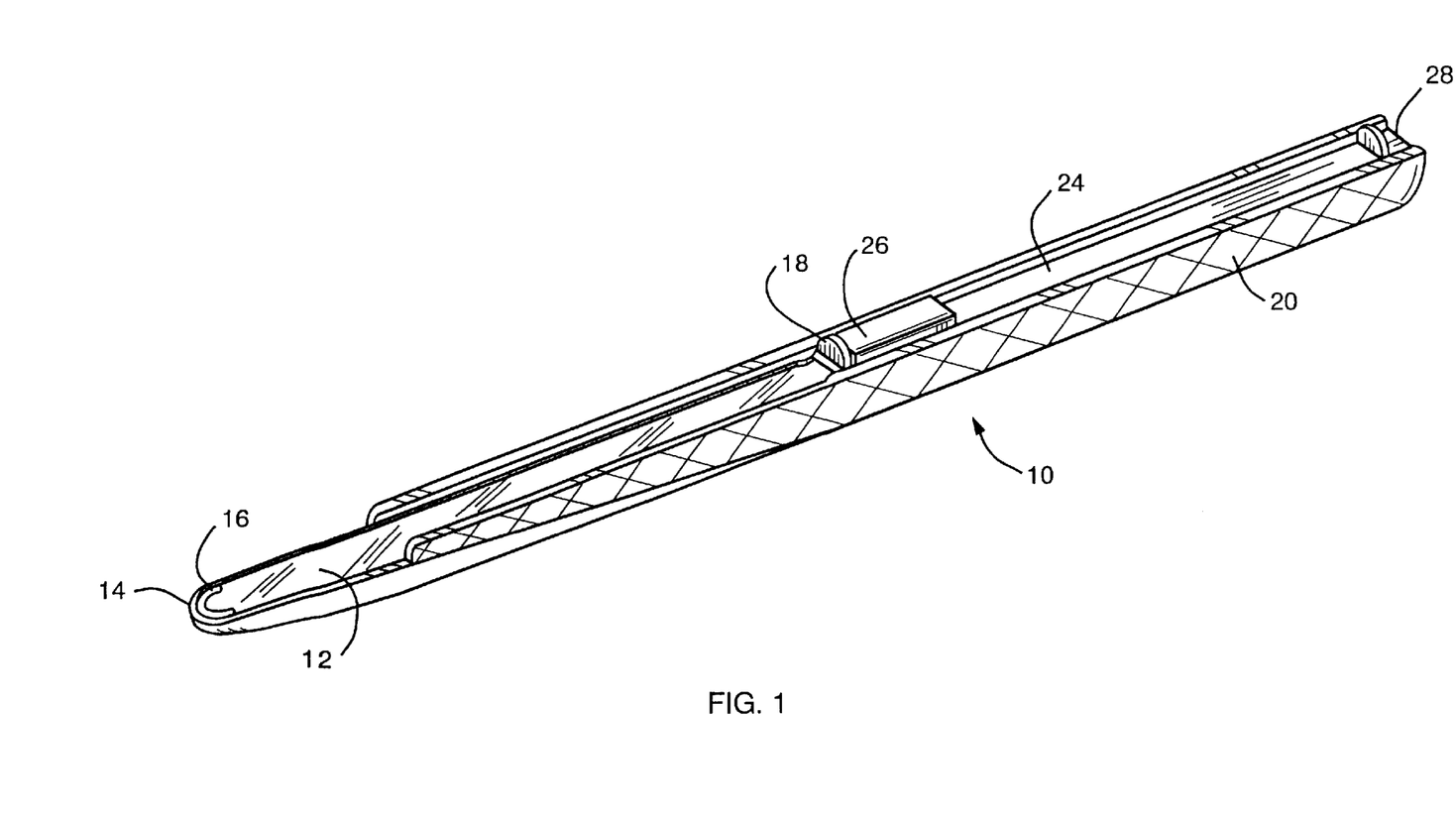
FIG. 1 is a perspective view of an associated instrument embodying the invention.

The general arrangement of the elements is shown most clearly in FIG. 1. This shows the assembly comprising the blade 12, the cutting edge 14, and aperture 16, a blade tab 18, the handle 20, a plunger 24, a lock button 26, and a plunger tab 28, all of which are discussed in more detail hereinafter.

Figure 4A:
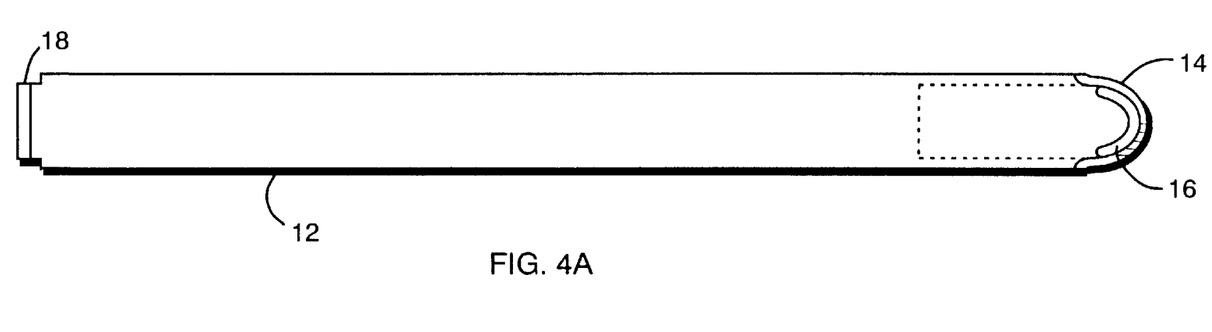
Figure 4B:
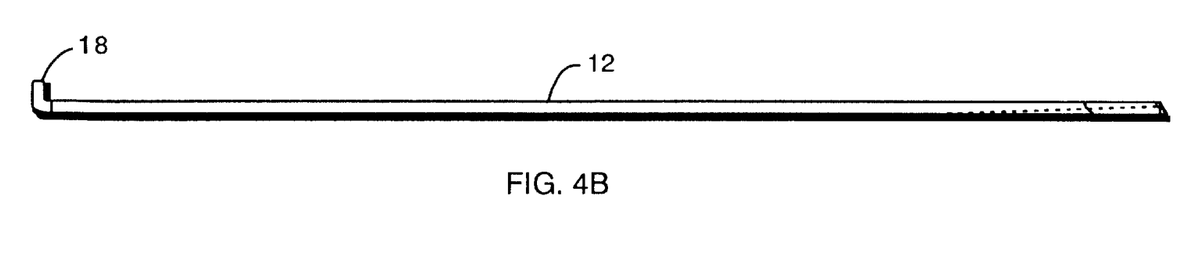
Figure 4C:
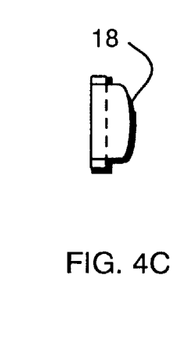

Referring now to FIGS. 4, there is shown a construction of a preferred form of the blade of the invention. This is an improved form of the cutting structure shown in FIGS. 18 and 19 of the parent application wherein a loop shaped curved cutting structure is formed on the distal end of the cutting blade 12. The curved structure of the preferred embodiment is a semi-circular cutting edge 14 formed by perforating the distal end of the blade 12 with a semi-circular hole 16. The back surface of the blade, i.e., the surface away from the one adjacent the bone structure, is preferably relieved at 13 between its edges so that the depth of the hole adjacent the cutting edge is equal to or less than the width of the hole 16. This provides easy transfer of the cut bone into the space behind the blade and prevents clogging of the hole during the cutting operation.

Figure 5A:
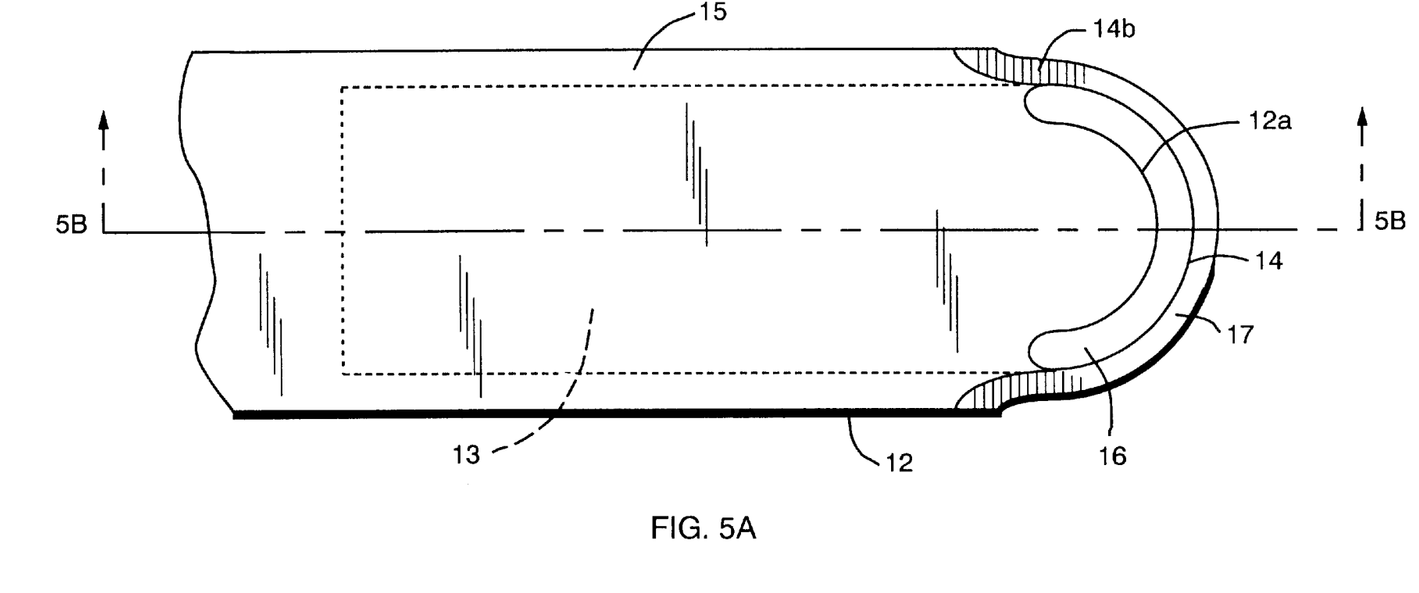
Figure 5B:
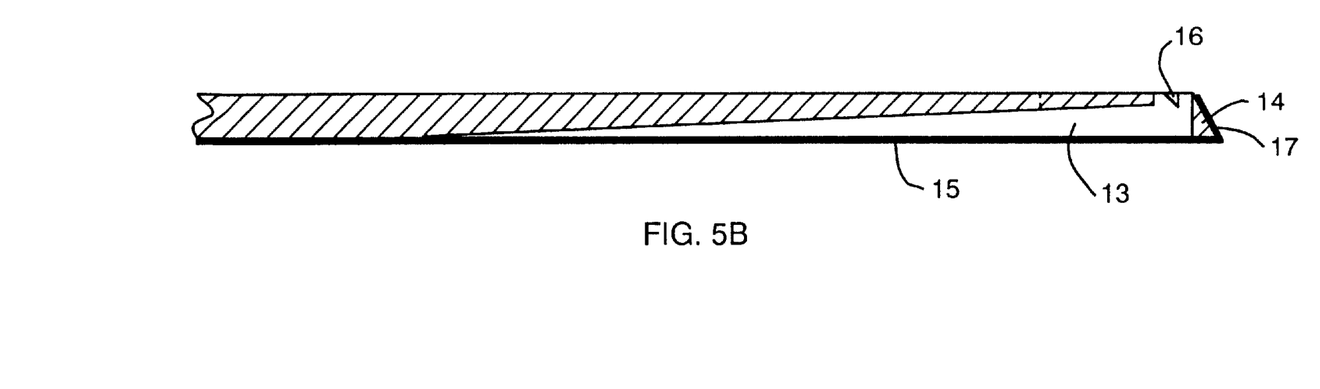

As seen in FIG. 5, the hole 16 in this preferred embodiment is essentially normal to the long dimension of the blade so that the inner side of the cutting edge is essentially normal to the face of the blade which contacts the bone. A slope 17 cooperates with hole 16 to define cutting edge 14. However, in use the blade is held at a slight angle to the bone, hence defined the working angle $\alpha_W$. The working angle of the instrument is equivalent to rake angle of the cutting edge with respect to the bone at the tip of the cutting edge 14, with an effective range of positive rake angles from about 5–50 degrees when the blade is mounted in the handle.

Curved Blade

Novel features of the blade allow manual cutting of the bone, with several advantages over motorized or pneumatic tools. These advantages include decreased costs, decreased set-up time, and decreased heat generation to optimize bone cell survival.

Figure 7A:
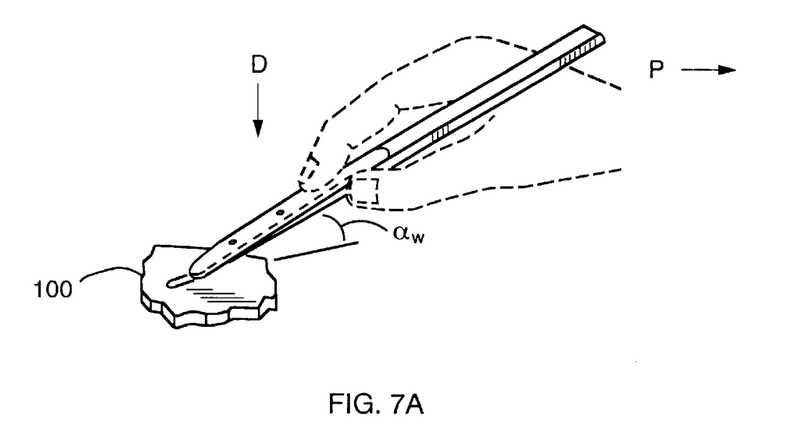
Figure 7B:
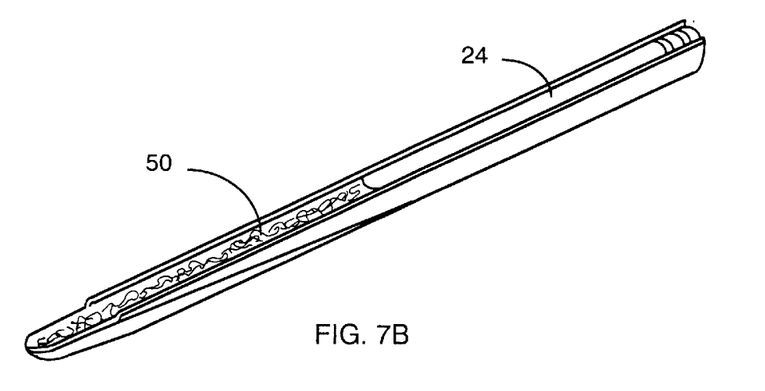
Figure 7C:
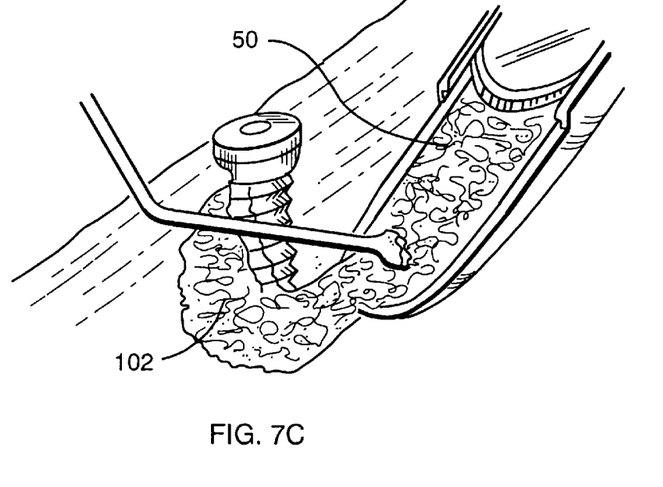

Controlled application The instrument is easily controlled in comparison to a osteotome or a gouge, where if these instruments disengage from the bone, they lunge into the tissue at the wound borders. With the pulling action of this design as shown in FIG. 7A, it is unlikely that the patient would be harmed if the blade inadvertently disengages from the bone. Furthermore, cutting can be carried safely to the boundary of the exposed bone with the blade naturally tracking a straight line without a tendency to veer off.

Figure 6:
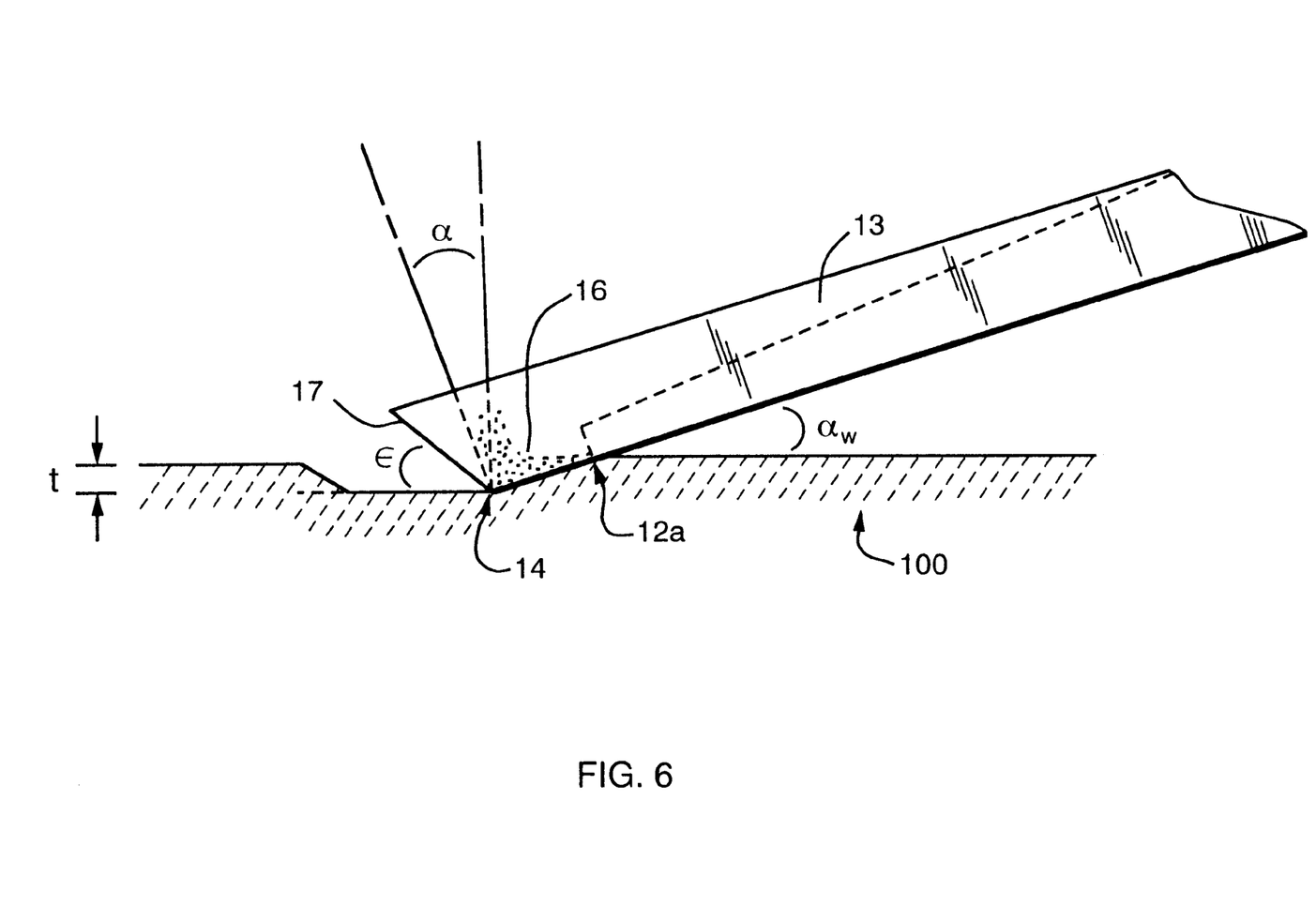
FIG. 6 is a diagrammatic illustration of the various angles involved in the cutting operation of the blade.

Variable rake angle The inner edge of the loop at its distal aspect 14 forms a positive rake angle with respect to the bone surface when the distal end is held in contact with, and at an acute angle to the bone. These various angles are illustrated in FIG. 6. Bone is an anisotropic material with varying requirements for cutting based on orientation. The rake angle of the blade edge can be modified by the working angle of the instrument to the bone surface. This allows adjustment of the cutting parameters of the blade for different bone properties. The Merchant analysis relates the effects of rake angle, depth, and material properties of isotropic materials as a function of a horizontal pulling force for cutting of a straight blade by:

$$Px = t_0 bt\cos(\beta-\alpha)/\sin\phi\cos(\phi+\beta+\alpha)$$

where:

$t_0$ = shear stress at failure on the shear zone (16,260 psi)
$\beta$ = friction angle = arc tan $\mu$(37°)
$\alpha$ = tool rake angle (5° –50°)
$\phi$ = shear plane angle (=34°, 2$\phi$+$\alpha$=90°)
b = work piece width (estimate 0.020 in)

t = nominal chip thickness (depth of cut, estimate 0.005 in))

$\mu$=friction coefficient between tool face and chip (0.75)

Substituting values into the equations with a rake angle of 30 degrees:

Px =16,260 psi ·0.020 ·0.005 ·cos (37° –30°) / sin 34°cos (34°+37 °–30°) =3.82 lbs This relationship is represented graphically for rake angles from 0–55 degrees as is illustrated in graph A below:

Theoretical results in comparison to experimental results are of limited agreement because of the anisotropic nature of bone. [Jacobs, C H, Pope, M H, Berry, J T, Hoaglund, F. A Study of the Bone Maching Process-Orthogonal Cutting J. Biomechanics, 7:131–136 1974]

Point Contact: As the working angle of the blade's curved loop is increased from zero degrees (full contact of the blade loop with the surface), only the point tangent to the loop's edge 14 remains in contact with the bone surface. Now only slight downward force on the instrument is necessary the cause very high pressures at the interface between the blade and the bone. This allows the blade to penetrate and engage the bone and allows the cut to be initiated. In addition, this point contact allows the blade to engage flat, convex, and most concave bone surfaces. In comparison to a straight or flat blade design where contact surface is not influenced by working angle, contact area is large with higher forces required to penetrate and engage the surface. In addition, cutting of concave surfaces is greatly limited. Approximation of the maximum contact pressure(s) between the blade loop and the bone surface can be estimated from one derivation of the H. Hertz equations for a cylinder on a flat plate of equal modulus:

$$s=0.591\sqrt{(P_1 E/d_{cyl})}$$

where $P_1$=load per inch length, E=modulus of elasticity, $d_{cyl}$=diameter of cylinder. For a 1 lb. load on the blade edge 0.001 in width and 0.25 in dia, and E for bone $2.61 \times 10^6$ psi:

$$s=0.591 \sqrt{[1000 * 2.61 \times 10^6/0.25]} =60,386 \text{ psi}$$

The modulus of stainless steel is about 10 fold greater than cortical bone, with these contact pressures conservatively less than steel in contact with bone. Cortical bone, with ultimate tensile stress of 20,300 psi, would be indented and engaged by the blade.

Contact stress for a range of blade edge thickness are illustrated below in graph B:

Cutting depth equilibrium: The blade allows smooth, uniform cutting of bone with minimal chatter. After engagement of the blade into the bone surface, its positive rake angle further promotes deeper engagement of the blade without increase in normal force. The diving force $F_d$ is a function of the pulling force parallel to the bone surface $F_p$ and the working angle of the instrument $\alpha_w$:

$$F_d = F_p \sin(\alpha_w)$$

The diving forces increase with the working angle of the instrument. Blade cutting depth reaches equilibrium. This is a function of the laterally decreasing rake angle from the central point of contact, the proximal edge 12A of the blade at the aperture 16, and a wedging effect caused by medial compression of the bone chip as it moves into the circular aperture 16. Geometrically, the aperture width $w_a$ and working angle of the instrument $\alpha_w$ limit the maximum depth of the dive d:

$$d = W_a \sin(\alpha_w)$$

Graphically, with an aperture width of 0.030 in, maximum cutting depth is shown in graph C:

Cutting with longitudinal and lateral movements Anatomic bone surfaces present a terrain of variable contour, with access to these surfaces also limited by adjacent anatomic structures and overlying tissue. The curved loop shaped blade, FIG. 5A, provides primary cutting along the longitudinal axis of the instrument. With the cutting edge at the distal end of the blade, this allows access under tissue flaps to the edge of the elevated periosteum. In addition, the blade can be moved laterally at is distal aspect to cut the bone surface in areas of limited access.

Cutting now occurs in the more lateral and proximal positions of the loop 19.

Edge material properties and surface The blade edge is hardened to approximately 58 Rockwell C (Brinell hardness~600 kg/mm$^2$) to prolong its cutting life. Cortical bone has harness 80 Rockwell M (Brinell hardness~30 kg/mm$^2$). Hardness can be further enhanced with titanium nitride coating which also decreases the interface friction between the blade and the bone. The hollow grind of the blade relief at 17 allows the edge profile to be thinner while optimizing the blade stiffness with support above the edge. The edge is both ground and honed in a direction perpendicular to the edge to minimize areas of stress concentration that can occur as the blade thins to its edge.

Narrow Semi-Circular Aperture Adjacent to Cutting Edge

Bone shavings pass through the narrow aperture 16 and can be collected for eventual grafting purposes. The aperture is analogous to a one way valve, where the shavings easily pass through in their dense form before their shapes and orientations become randomized. This randomized form of the bone is favorable. It prevents the bone shavings from falling back through the aperture 16 and thus not being available for grafting. It allows the shavings to be collected without the use of vacuum which both desiccates and necroses the bone cells, and potentially contaminates the bone with saliva and soft tissue elements.

The bone shavings or chips have favorable properties with respect to their application as autogenous bone grafts. These include an increase in their surface area to volume ratio, an increase in the relative volume of bone, and a porosity that allows incorporation of blood and encourages vascular ingrowth and cell migration into the graft. The exposed collagen promotes coagulation of the blood elements and renders the graft in a favorable "mortar-like" consistency to be packed into the defect sites in the form of an osseous coagulum.

As mentioned previously, the distal end of the upper aspect of the blade incorporates a central ramp or tapered reduced thickness 13, with the proximal end of the ramp decreasing in thickness to where it ends at 12A adjacent the blade aperture 16. This reduced section is shown best in FIG. 5B and has the function of providing a very thin blade section 12A immediately adjacent the rear of the hole 16. The blade thickness is maintained laterally with a ridge and sidewalls 15 adjacent to the ramp. This allows the blade loop to have the thickness required for strength, while providing a very short path through the aperture 16. This short passage reduces the chances of clogging.

The ramp 13 serves several additional functions. It provides an initial storage area for the shavings as they are collected. It provides an increase in the cross-sectional area of the reservoir that allows the handles external profile to be reduced in height and thus more accessible to constrained anatomic locations.

Figures 8A, 8B, 8E:
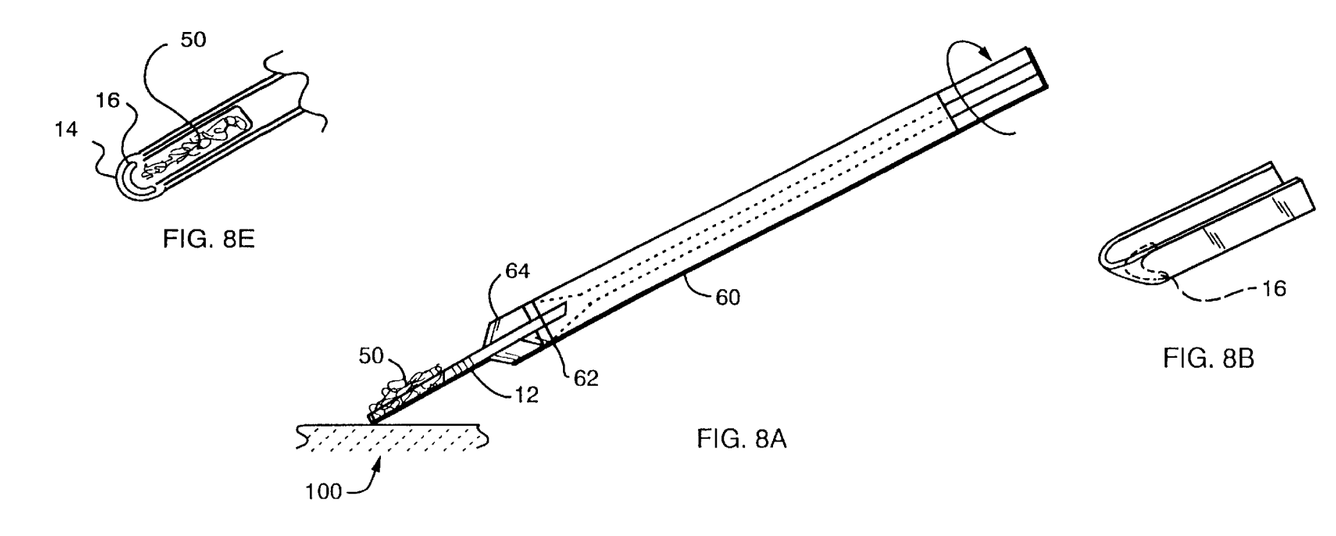
FIGS. 8A–8F illustrate a modified version of handle and bone collection systems.
Figure 8C:
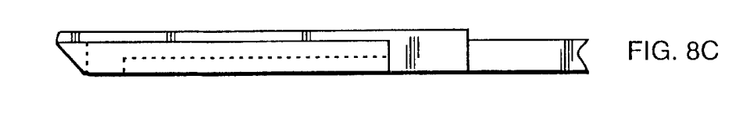
Figure 8D:
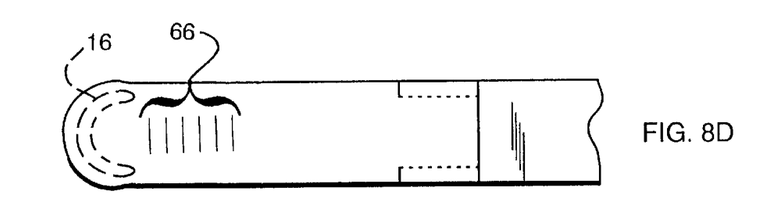
Figure 8F:
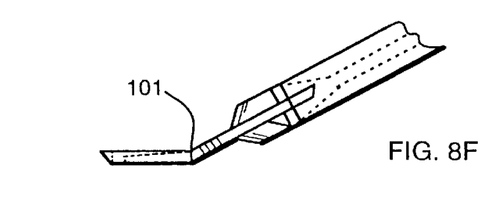

When the handle for the blade does not incorporate the storage area (as shown in FIG. 8*a*), the ramp 13 provides a seat for the bone as it is collected as shown in FIGS. 8a–b. A small collection chamber, not integral to the handle, can also be attached to the blade's upper surface as shown in FIG. 8c. Finally, in concert with the handle chamber geometry, the chamber is designed with increasing cross-sectional area as one moves proximally, encouraging the chips to move into the handle proximally as the bone is collected.

The blade is preferably bowed longitudinally to create a spring that provides friction between the blade and the grooves 40 of the side wall 30 of the handle 20. This keeps the blade in the desired position until it intentionally needs to be shifted. With the variability in manufacturing, the longitudinal bow geometry allows a relatively large amount of deflection to be used, which makes dimensional variation in production inconsequential. Also, steel, as opposed to the plastic used in the handle, has a predictable modulus of elasticity that will not creep.

As seen best in FIGS. 1 and 4, at the rear of the blade 12 there is provided a blade tab 18 which is adapted to be engaged to a lock button 26 on the end of the plunger 24 (see FIGS. 1 and 3) which is mounted in the handle 20 proximal of the blade 12. The extended length of the tab 18 from the cutting edge (as shown in FIG. 4A) allows the tab 18 to transmits the raking force from the center of the handle where it has sufficient strength. Furthermore, manipulation of the blade is controlled safely away from the sharp edge. Finally, the extended length blade also serves as a 4th moveable wall of the collection chamber. This allows for a very compact design capable of being used in tight places and allows easy access to the contents of the chamber.

As seen best in FIG. 8, for constrained anatomic sites, the blade may used with just a gripping handle attached to its proximal end. This leaves the upper surface of the blade exposed on its mid and distal aspects. This allows the blade access to more constrained anatomic locations and also allows the blade to be bent and offset to optimize its access to more specific anatomic locations. The blade can also be increased in thickness to provide more volume in its central ramped hollow to collect the bone shavings.

Figure 2A:
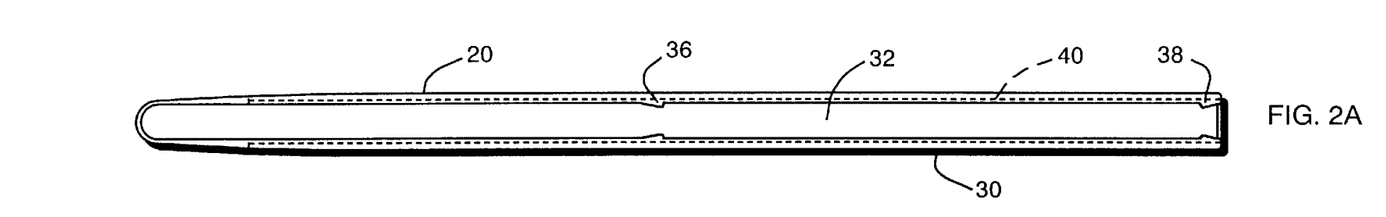
Figure 2B:
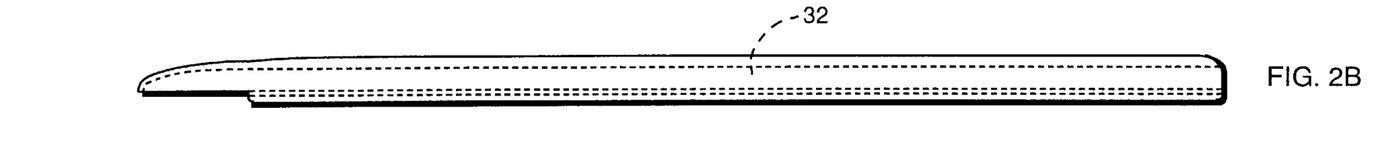
Figure 2C:
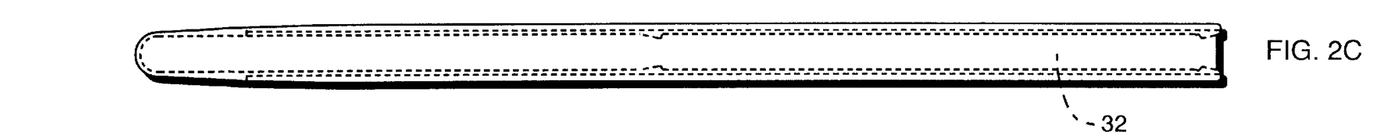
Figure 2D:
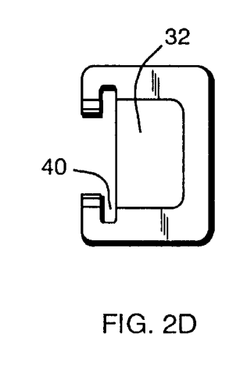
Figure 2E:
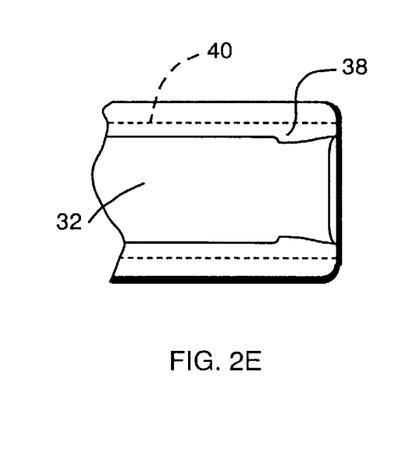
Figure 2F:
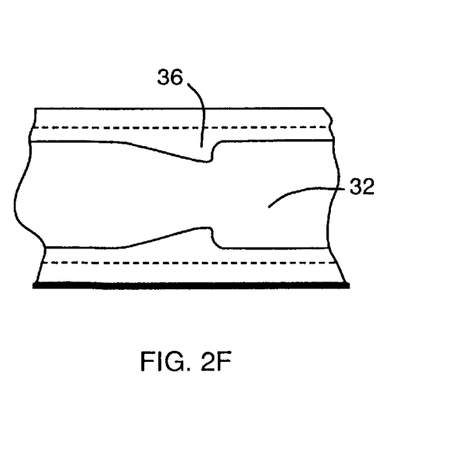
Figure 3A:
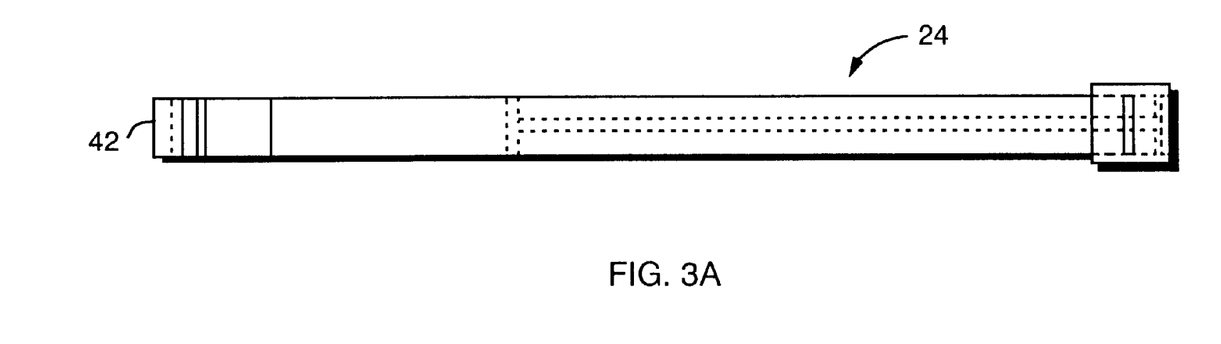
Figure 3B:
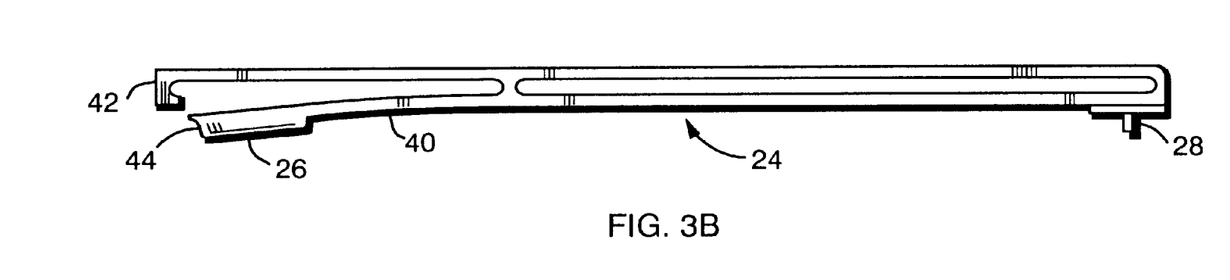
Figure 3C:
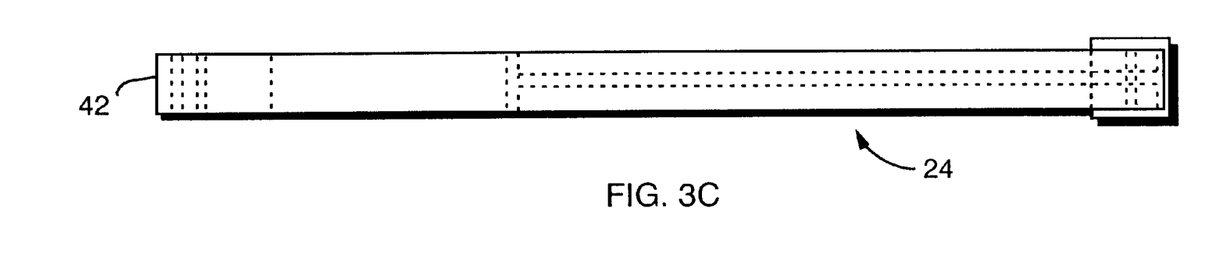
Figure 3D:
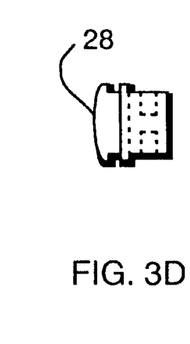

The details of the handle 20 are shown best in FIG. 2 wherein side wall 30 and bottom wall 32 define a u-shaped space as seen best in FIG. 2A. There are two sets of detents, the first set 36 are positioned to engage the tab on the rear end of the blade to prevent its moving beyond the end of the handle 20. The second set 38 are positioned to engage the plunger tab 28 on the plunger 24 and retain the plunger in the position shown FIG. 1 with the lock button 26 in engagement with the blade tab.

The handle of the preferred embodiment serves multiple functions, integrating ergonomic handling and support of the blade, a storage compartment or reservoir of the collected bone, a site for combining additives as needed, and a means of delivering and dispensing the harvested bone at the recipient site. This integrated function also minimizes bone waste and possible contamination by minimizing handling of the bone and the accumulation of the graft material on surfaces such as hoses, filters, containers, etc.

The handle provides safe and clean storage of the harvested bone. After passing through the blade aperture 16 the bone enters a closed storage space formed by the handle in conjunction with the blade and the plunger. This space expands in cross-section area as it approaches the proximal aspect of the ramp, encouraging the bone shaves to move into the proximal aspect of the handle. The handle interior provides a trough shaped volume where the contents can be inspected, additives incorporated, and any possible clogging of bone cleared. The plunger 24 can be advanced to consolidate the harvested bone with the blade fully forward. With the blade partially retracted, the plunger advances the graft material to the distal aspect of the handle to provide a streamline trough or channel to deliver bone to the recipient site.

The preferred profile for the forward portion of the handle is minimized by transmitting the raking force from the handles center, its thicker and stronger portion. Only a small amount of handle material is required for sufficient strength to carry the normal load to the nose of the handle. This results in a low instrument profile, capable of getting into anatomic spaces of limited dimension. A single pair of grooves 40 guide and retain both the blade and the plunger. This helps to minimize the overall height of the handle.

Also, as shown in FIG. 8C, the handle is preferably fabricated with a clear plastic. This allows the bone shavings to be monitored as they are cut, providing immediate feedback of bone collection. The total volume of bone collected can be monitored with respect to known volume gradations 66 on the handle that inform the surgeon when an adequate volume of bone has been collected.

When the blade is used such that middle and distal portions are exposed, a gripping handle 60 is secured to the proximal end of the blade to facilitate handling of the blade as shown in FIG. 8A. The handle 60 is long and round for secure gripping in the hand and has a slot 62 to accept the blade and a tightening mechanism 64 to secure the blade in the handle.

The plunger 24 serves two functions; 1) to consolidate and advance the bone into the distal end of the chamber, and 2) it provides a locking mechanism to secure the blade in its forward position.

The plunger head 42 provides the proximal wall of the storage chamber. The plunger is advanced by releasing the locking button 26 which secures both the plunger and the blade in place for cutting and collection. The head of the plunger is held in the track distally by riding under the blade. The proximal end is constrained in the same track 40 that the blade rides in and translates forward to a small stop at the forward end of the handle.

Referring to FIG. 3, the details of the plunger are shown in top view and sectional view wherein the lock button 26 as shown as being mounted on a cantilever arm 46 enabling it to be moved towards the bottom of the plunger. The side edges of the plunger are free of the grooves 40 in the side wall of the handle. The sloping surface 44 on the detent arm 40 engages the proximal end of the blade to press the blade tab 18 against the detents 36, thus locking the blade in correct position.

We claim:

1. An instrument for harvesting bone comprising an elongate body having a proximal end and distal end; said body serving as a handle for the instrument, and supporting a blade therein so that the blade can be held at an acute angle with respect to a bone from which bone shavings are to be harvested;

said blade comprising an elongate flat member having a cutting structure adjacent its distal end;

the cutting edge of the structure being defined by a curved hole adjacent the distal end of the blade and a tapered curved convex surface forming the distal end of the blade;

said blade and handle cooperating to provide a storage space adjacent the distal end of the blade for receiving harvested bone from the cutting structure; and a plunger slidably mounted in the handle for consolidating bone shavings in the storage space and for dispensing bone shavings at the distal end of the instrument;

wherein said handle is channel shaped, having a longitudinal opening which creates a central storage space within said channel, and said plunger provides moveable access to said space, and further comprising a track running along the upper aspect of each side of the channel to secure and allow movement of the blade and plunger.

2. The instrument in claim 1, wherein the blade has a loop shaped cutting structure adjacent its distal end, which loop forms a positive rake angle with respect to the bone surface when said distal end is held in contact with, and at an angle to, the bone.

3. The instrument of claim 1, wherein the blade has a reduced thickness immediately adjacent the inner edge of the curved hole.

4. The instrument in claim 3, wherein said reduced thickness is less than the radial width of the curved hole.

5. The instrument in claim 3, wherein the outer section of the blade is of full thickness to provide a force-transmitting structure for the end of the curved blade.

6. The instrument of claim 3, wherein the reduced thickness immediately adjacent the inner edge of the curved hole is a ramp-like depression centrally positioned in the blade.

7. The instrument of claim 6, wherein the central depression provides a storage area for the bone shavings.

8. The instrument of claim 7, wherein a hollow structure is attached to the blade over the central depression to provide a storage chamber of greater volume than the central depression for storage of the bone shavings.

9. The instrument in claim 2, wherein the relative rake angle of the cutting edge with respect to the bone decreases as the contact area extends proximal along the curved edge.

10. The instrument of claim 1, wherein the blade has a tab adjacent its proximal end for transmitting cutting forces to the central portion of the handle.

11. The instrument of claim 1, wherein the handle is of an ergonomic streamline shape, with a shallow distal profile for accessing greatly narrowed spaces.

12. The instrument of claim 1, wherein the handle is composed of a clear plastic that provides visual feedback of the progress in collecting the bone shavings.

13. The instrument of claim 12, wherein graduations are present to provide indication of the volume of material collected.

14. The instrument of claim 1, wherein said storage space defined by the blade and handle expands in cross-sectional area from the distal end to proximal aspect of the handle to encourage flow of bone chips into the handle and away from the blade edge.

15. The instrument of claim 1, and further comprising detents and/or protrusions adjacent to said track for providing stops for positioning the blade and the plunger.

16. The instrument of claim 1, wherein the plunger also provides a self-adjusting locking mechanism for firmly securing the blade in its distal position when the instrument is in cutting function.

17. The instrument of claim 1, wherein the blade is bowed longitudinally to provide friction for the blade in the track.

18. The of claim 1, wherein the blade and the handle are one piece.

19. An instrument for harvesting bone comprising an elongate body having a proximal end and distal end; said body serving as a handle for the instrument, and supporting a blade therein so that the blade can be held at an acute angle with respect to a bone from which bone shavings are to be harvested;

said blade comprising an elongate flat member having a cutting structure adjacent its distal end;

the cutting edge of the structure being defined by a curved hole adjacent the distal end of the blade and a tapered curved convex surface forming the distal end of the blade;

said blade and handle cooperating to provide a storage space adjacent the distal end of the blade for receiving harvested bone from the cutting structure, a plunger incorporated into the handle for consolidating bone shavings in the storage compartment for dispensing at the distal end of the instrument, and further comprising a lock button provided on the distal end of the plunger, the distal end of the lock button engaging the proximal end of a tabbed blade.

20. The instrument of claim 19, wherein the lock button is carried on the end of a spring arm which permits compression of the lock button into the groove to release the blade tab whereby to permit the blade to be withdrawn in the proximal direction and thereby permit the plunger to be pushed towards the distal end of the handle to contact bone particles stored in the handle.

21. The instrument of claim 19, wherein the lock button is positioned proximally of the plunger.

* * * * *